United States Patent [19]

Pawloski

[11] Patent Number: 4,568,759

[45] Date of Patent: Feb. 4, 1986

[54] PREPARATION OF EPOXIDES

[75] Inventor: Chester E. Pawloski, Bay City, Mich.

[73] Assignee: The Dow Chemical Company, Midland, Mich.

[21] Appl. No.: 587,476

[22] Filed: Mar. 8, 1984

[51] Int. Cl.$^4$ .......................................... C07D 301/02
[52] U.S. Cl. .................................... 549/518; 260/463
[58] Field of Search ......................................... 549/518

[56] References Cited

U.S. PATENT DOCUMENTS

| | | | |
|---|---|---|---|
| 2,022,182 | 11/1935 | Britton et al. | 549/518 |
| 2,248,635 | 7/1941 | Marple et al. | 549/521 |
| 2,756,242 | 7/1956 | Riener | 549/518 |
| 2,860,146 | 11/1958 | Furman et al. | 549/521 |
| 3,388,078 | 6/1968 | Evans et al. | 549/518 |
| 4,261,906 | 4/1981 | Renga et al. | 549/518 |

FOREIGN PATENT DOCUMENTS

| | | | |
|---|---|---|---|
| 57-026677 | 2/1982 | Japan | 549/518 |
| 193478 | 3/1967 | U.S.S.R. | 549/518 |

OTHER PUBLICATIONS

CA 59:7491c; 64:1958g; 88:37242y; 92:110822b; 71:81124j; 59:12643e; 67:11425b; 70:68112p.
Carl R. Noller, Chemistry of Organic Compounds (1965) 3rd Ed., pp. 332–333.
A. Weissberger, Heterocyclic Compounds with Three- and Four-Membered Rings, Part One (1964) pp. 94–98.

Primary Examiner—Norma S. Milestone

[57] ABSTRACT

This invention is a process for the preparation of an epoxide which comprises contacting a 2-haloalkyl or 2,3-dihaloalkyl carbonate, bis(2-haloalkyl- or 2,3-dihaloalkyl)carbonate, or 2-haloalkyl or 2,3-dihaloalkyl ester dissolved in a water-miscible alcohol with a sufficient amount of an aqueous solution of an alkali metal or alkaline earth metal hydroxide to provide at least one equivalent of alkali metal or alkaline earth metal hydroxide per equivalent of ester or carbonate, at a temperature of between about 0° C. and 70° C. under conditions such that an epoxide is prepared.

15 Claims, No Drawings

1

PREPARATION OF EPOXIDES

BACKGROUND OF THE INVENTION

This invention relates to the preparation of epoxides.

Vicinal epoxides are valuable chemical intermediates and monomers useful in making epoxy adhesives and various heat- and solvent-resistant polymers. A well-known process for making vicinal epoxides from olefins involves the oxidation of the olefinic double bond with aqueous chlorine to form the chlorohydrin and reaction of the chlorohydrin with a base to make the epoxide. However, a major disadvantage of this process is the production of an equivalent of HCl from the aqueous oxychlorination step and another equivalent of inorganic chloride from the reaction of the base with the chlorohydrin intermediate. In the case of epichlorohydrin, the conventional preparation uses the same chemistry with the added initial step of chlorinating propylene to allyl chloride which produces an additional equivalent of HCl.

Ethylene oxide is prepared by oxidizing ethylene with molecular oxygen over a silver catalyst. However, this method is not applicable to other olefins because of low selectivity and the formation of by-products. Another method using oxygen involves oxidizing a hydrocarbon such as isobutane or isopropylbenzene with air to the corresponding tertiary hydroperoxide and then reacting the hydroperoxide with an olefin in the presence of a transition metal catalyst. A disadvantage of this process is the formation of co-product alcohol which must be sold or recycled.

Hydrogen peroxide and peroxy acids are other reagents which have been used to epoxidize olefins. Chemical and economic disadvantage of such methods have precluded their use on a large scale.

It is known that cyclic carbonates can be decomposed to form epoxides in the presence of various catalysts. Such a process particularly directed to the preparation of propylene oxide by decomposition of propylene carbonate in the presence of a sulfonium or phosphonium halide or any of certain metal salts is described in U.S. Pat. No. 4,069,234.

U.S. Pat. No. 4,261,906 discloses a process for the preparation of vicinal epoxides by heating an unsymmetrical β-haloalkyl carbonate in the presence of a small but effective amount of a quaternary ammonium or phosphonium salt at a temperature of about 25° C. to 250° C. U.S. Pat. No. 4,069,234 discloses the preparation of vicinal epoxides by heating a corresponding alkylene carbonate in the presence of a catalytic amount of a catalyst selected from the group consisting of phosphonium halides, sulfonium halides, sulfoxonium halides, and certain metal salts.

Many of the methods described hereinabove for the preparation of epihalohydrins, involve the reaction of a base with a 2,3-dihalopropanol. Such 2,3-dibromopropanol is prepared by the halogenation of an allyl alcohol, which produces the undesirable by-product, 1,2,3-tribromopropane. The reaction of this undesirable by-product with a base produces 2,3-dibromopropene, which is difficult to separate by distillation from epibromohydrin.

What is needed is a process for the preparation of halohydrins in which no hydrogen halide by-product is prepared. What is further needed is a process in which unwanted by-products, such as 2,3-dibromopropene, are not prepared.

SUMMARY OF THE INVENTION

This invention is a process for the preparation of an epoxide which comprises contacting a 2-haloalkyl or 2,3-dihaloalkyl carbonate, bis(2-haloalkyl- or 2,3-dihaloalkyl)carbonate, or 2-haloalkyl or 2,3-dihaloalkyl ester dissolved in a water-miscible alcohol with a sufficient amount of an aqueous solution of an alkali metal or alkaline earth metal hydroxide to provide at least one equivalent of alkali metal hydroxide or alkaline earth metal hydroxide per equivalent of ester or carbonate, at a temperature of between about 0° C. and 70° C. under conditions such that an epoxide is prepared.

This invention results in a process in which epoxides are prepared wherein no hydrogen halide or unwanted by-products are produced.

DETAILED DESCRIPTION OF THE INVENTION

Carbonates useful in this invention are those which contain at least one alkyl group which is substituted in the 2 position with a halogen. Among such carbonates are 2-haloalkyl carbonates, 2,3-dihaloalkyl carbonates, bis(2-haloalkyl)carbonates, and bis(2,3-dihaloalkyl)carbonates.

Esters in this invention include those in which the alkyl group attached to the oxygen moiety contains a halogen substituent on the 2 carbon. Examples of such esters are 2-haloalkyl ester and 2,3-dihaloalkyl esters.

The 2-haloalkyl- or 2,3-dihaloalkyl carbonate and the bis(2-haloalkyl- or 2,3-dihaloalkyl)carbonate preferably corresponds to the formula

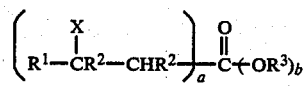

wherein $R^1$ is separately in each occurrence

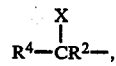

hydrogen, $C_{1-20}$ hydrocarbyl or $C_{2-20}$ hydrocarbyloxyhydrocarbyl;

$R^2$ is separately in each occurrence hydrogen or $C_{1-20}$ hydrocarbyl;

$R^3$ is separately in each occurrence $C_{1-20}$ hydrocarbyl;

$R^4$ is separately in each occurrence hydrogen, $C_{1-20}$ hydrocarbyl or $C_{2-20}$ hydrocarbyloxyhydrocarbyl;

X is separately in each occurrence chlorine, bromine or iodine;

a is 1 or 2; and b is 0 or 1;

with the proviso that the sum of a and b is 2.

The 2-haloalkyl esters and 2,3-dihaloalkyl esters preferably correspond to the formula

wherein $R^1$, $R^2$, $R^3$, $R^4$ and X are as defined hereinbefore.

In one preferred embodiment, the carbonate is a 2,3-dihaloalkyl carbonate or a bis(2,3-dihaloalkyl)carbonate. These compounds correspond to the formula

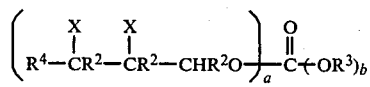

wherein $R^1$, $R^2$, $R^3$, $R^4$ and X are as hereinbefore defined.

The 2,3-dihaloalkyl esters generally correspond to the formula

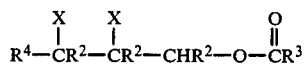

wherein $R^2$, $R^3$, $R^4$ and X are as hereinbefore defined.

In a preferred embodiment, the 2-haloalkyl carbonates are preferred as starting reactants over the 2-haloalkyl esters.

In the above formulas, $R^1$ is preferably

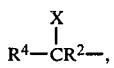

hydrogen, $C_{1-20}$ alkyl, $C_{6-20}$ aryl, $C_{7-20}$ alkaryl, $C_{7-20}$ aralkyl or $C_{2-20}$ alkoxyalkyl. $R^1$ is more preferably

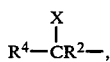

hydrogen, $C_{1-10}$ alkyl, $C_{6-10}$ aryl, $C_{7-10}$ alkaryl, $C_{7-10}$ aralkyl or $C_{2-10}$ alkoxyalkyl. $R^1$ is even more preferably

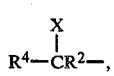

hydrogen, $C_{1-4}$ alkyl, phenyl or benzyl. $R^1$ is even more preferably

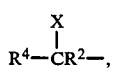

hydrogen or methyl. $R^1$ is most preferably

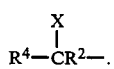

$R^2$ is preferably hydrogen or $C_{1-20}$ alkyl. $R^2$ is more preferably hydrogen or $C_{1-3}$ alkyl. $R^2$ is even more preferably hydrogen or methyl. $R^2$ is most preferably hydrogen.

$R^3$ is preferably $C_{1-20}$ alkyl, $C_{6-20}$ aryl, $C_{7-20}$ alkaryl or $C_{7-20}$ aralkyl. $R^3$ is more preferably $C_{1-10}$ alkyl, $C_{6-10}$ aryl, $C_{7-10}$ alkaryl or $C_{7-10}$ aralkyl. $R^3$ is most preferably $C_{1-3}$ alkyl, phenyl or benzyl.

$R^4$ is preferably hydrogen, $C_{1-20}$ alkyl, $C_{6-20}$ aryl, $C_{7-20}$ alkaryl, $C_{7-20}$ aralkyl or $C_{2-20}$ alkoxyalkyl. $R^4$ is more preferably hydrogen, $C_{1-10}$ alkyl, $C_{6-10}$ aryl, $C_{7-10}$ alkaryl, $C_{7-10}$ aralkyl or $C_{2-10}$ alkoxyalkyl. $R^4$ is even more preferably hydrogen, $C_{1-4}$ alkyl, phenyl or benzyl. $R^4$ is most preferably hydrogen or methyl.

$C_{1-20}$ hydrocarbyl means herein an organic radical containing between one and twenty carbon atoms to which are bonded hydrogen atoms. Included are the following groups: $C_{1-20}$ alkyl, $C_{1-20}$ alkenyl, $C_{1-20}$ alkynyl, $C_{3-20}$ cycloalkyl, $C_{3-20}$ cycloalkenyl, $C_{6-20}$ aryl, $C_{7-20}$ alkaryl or $C_{7-20}$ aralkyl.

The term aryl refers herein to biaryl, phenyl, naphthyl, phenanthranyl and anthranyl. Alkaryl refers herein to an alkyl-, alkenyl- or alkynyl-substituted aryl substituent wherein aryl is as defined hereinbefore. Aralkyl means herein an alkyl, alkenyl or alkynyl substituent substituted with an aryl group, wherein aryl is as defined hereinbefore.

$C_{3-20}$ cycloalkyl refers to an alkyl group containing one, two, three or more cyclic rings. $C_{3-20}$ cycloalkenyl referss to mono-, di- and polycyclic groups containing one or more double bonds. $C_{3-20}$ cycloalkenyl also refers to the cycloalkenyl groups wherein two or more double bonds are present.

The term hydrocarbyloxyhydrocarbyl refers herein to a moiety in which two hydrocarbyl moieties are connected by an oxygen atom, so as to form an ether functionality. A hydrocarbyloxyhydrocarbyl moiety can be represented by the formula —$R^5OR^6$ where $R^5$ is a hydrocarbylene moiety and $R^6$ is a hydrocarbyl moiety. A preferred hydrocarbyloxyhydrocarbyl moiety is an alkoxy alkyl moiety, that is wherein $R^5$ is an alkylene moiety and $R^6$ is an alkyl moiety.

X is preferably chlorine or bromine.

Examples of 2,3-dihaloalkyl carbonates include 2,3-dichloropropyl methyl carbonate, 2,3-dichloropropyl ethyl carbonate, 2,3-dichloropropyl propyl carbonate, 2,3-dichloropropyl phenyl carbonate, 2,3-dichloropropyl benzyl carbonate, 2,3-dibromophenyl methyl carbonate, 2,3-dibromopropyl ethyl carbonate, 2,3-dibromopropyl propyl carbonate, 2,3-dibromopropyl phenyl carbonate, 2,3-dibromopropyl benzyl carbonate, bis(2,3-dichloropropyl)carbonate, bis(2,3-dibromopropyl)carbonate, 2,3-dichlorobutyl methyl carbonate, 2,3-dichlorobutyl ethyl carbonate, 2,3-dichlorobutyl propyl carbonate, 2,3-dichlorobutyl phenyl carbonate, 2,3-dichlorobutyl benzyl carbonate, 2,3-dibromobutyl methyl carbonate, 2,3-dibromobutyl ethyl carbonate, 2,3-dibromobutyl propyl carbonate, 2,3-dibromobutyl phenyl carbonate, 2,3-dibromobutyl benzyl carbonate, bis(2,3-dibromobutyl)carbonate and bis(2,3-dichlorobutyl)carbonate. 2-Haloalkyl carbonates useful in this invention include 2-bromopropyl methyl carbonate, 2-bromopropyl ethyl carbonate, 2-bromopropyl propyl carbonate, 2-bromopropyl phenyl carbonate, 2-bromopropyl benzyl carbonate, 2-chloropropyl methyl carbonate, 2-chloropropyl ethyl carbonate, 2-chloropropyl propyl carbonate, 2-chloropropyl phenyl carbonate, 2-chloropropyl benzyl carbonate, 2-chloroethyl methyl carbonate, 2-chloroethyl ethyl carbonate, 2-chloroethyl propyl carbonate, 2-chloroethyl phenyl carbonate, 2-chloroethyl benzyl carbonate, 2-bromoethyl methyl carbonate, 2-bromoethyl ethyl carbonate, 2-bromoethyl propyl carbonate, 2-bromoethyl phenyl carbonate, 2-bromoethyl benzyl carbonate, 2-chlorobutyl methyl carbonate, 2-chlorobutyl ethyl carbonate, 2-chlorobutyl propyl carbonate, 2-chlorobutyl phenyl carbonate, 2-chlorobutyl benzyl carbonate, 2-bromobutyl methyl carbonate, 2-bromobutyl ethyl carbonate, 2-bromobutyl propyl carbonate, 2-bromobutyl phenyl carbonate, and 2-bromobutyl benzyl carbonate.

2-Haloalkyl esters useful in this process include 2-chloroethyl ethanoate, 2-chloroethyl propanoate, 2-chloroethyl butanoate, 2-chloroethyl benzoate, 2-chloroethyl 2-phenyl ethanoate, 2-bromoethyl ethanoate, 2-bromoethyl propanoate, 2-bromoethyl butanoate, 2-bromoethyl benzoate, 2-bromoethyl 2-phenyl ethanoate, 2-chloropropyl ethanoate, 2-chloropropyl propanoate, 2-chloropropyl butanoate, 2-chloropropyl benzoate, 2-chloropropyl 2-phenyl ethanoate, 2-bromopropyl ethanoate, 2-bromopropyl propanoate, 2-bromopropyl butanoate, 2-bromopropyl benzoate, 2-bromopropyl 2-phenyl ethanoate, 2-chlorobutyl ethanoate, 2-chlorobutyl propanoate, 2-chlorobutyl butanoate, 2-chlorobutyl benzoate, 2-chlorobutyl 2-phenyl ethanoate, 2-bromobutyl ethanoate, 2-bromobutyl propanoate, 2-bromobutyl butanoate, 2-bromobutyl benzoate, and 2-bromobutyl 2-phenyl ethanoate. The 2,3-dihaloalkyl esters which are useful in this process include 2,3-dichloropropyl ethanoate, 2,3-dichloropropyl propanoate, 2,3-dichloropropyl butanoate, 2,3-dichloropropyl benzoate, 2,3-dichloropropyl 2-phenyl ethanoate, 2,3-dibromopropyl ethanoate, 2,3-dibromopropyl propanoate, 2,3-dibromopropyl butanoate, 2,3-dibromopropyl benzoate, 2,3-dibromopropyl 2-phenyl ethanoate, 2,3-dichlorobutyl ethanoate, 2,3-dichlorobutyl propanoate, 2,3-dichlorobutyl butanoate, 2,3-dichlorobutyl benzoate, 2,3-dichlorobutyl 2-phenyl ethanoate, 2,3-dibromobutyl ethanoate, 2,3-dibromobutyl propanoate, 2,3-dibromobutyl butanoate, 2,3-dibromobutyl benzoate, and 2,3-dibromobutyl 2-phenyl ethanoate.

Hydroxides useful in this invention include alkali metal hydroxide and alkaline earth metal hydroxides. Examples of such hydroxides include sodium hydroxide, potassium hydroxide, calcium hydroxide, magnesium hydroxide, lithium hydroxide, beryllium hydroxide, rubidium hydroxide, strontium hydroxide, cesium hydroxide and barium hydroxide. Preferred hydroxides are the alkali metal hydroxides with sodium hydroxide and potassium hydroxide being the most preferred.

The product produced by the process of this invention is an epoxide, which includes those compounds which correspond to the formula

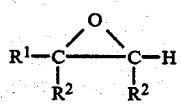

wherein $R^1$, $R^2$ and X are as defined hereinbefore.

In one preferred embodiment, the product is an α-haloalkyl epoxide. Included among α-halo epoxides are those which correspond to the formula

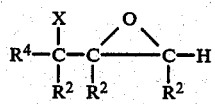

wherein $R^4$, $R^2$ and X are as defined hereinbefore.

The α-haloalkyl epoxides are prepared when the starting carbonate is a 2,3-dihaloalkyl carbonate, a bis(2,3-dihaloalkyl)carbonate or a 2,3-dihaloalkyl ester.

In another more preferred embodiment, the product is an epihalohydrin. The epihalohydrins are prepared wherein the starting compound is a 2,3-dihalopropyl carbonate, a 2,3-dihalopropyl ester or a bis(2,3-dihalopropyl)carbonate.

Examples of compounds prepared by this process include ethylene oxide, propylene oxide, 1,2-butylene oxide, epibromohydrin and epichlorohydrin.

This process in general involves contacting an ester or carbonate described hereinbefore dissolved in a water-miscible alcohol with an alkali metal hydroxide or alkaline earth metal hydroxide dissolved in water under conditions such that an epoxide is prepared. This process can be illustrated by equation 1 wherein a carbonate is the starting reactant.

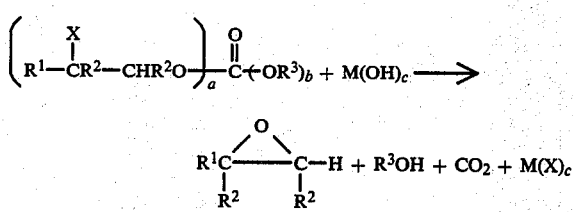

wherein $R^1$, $R^2$, $R^3$, X, a and b are as hereinbefore defined, and c is 1 or 2.

The process can be illustrated, wherein the starting reactant is an ester, by equation 2,

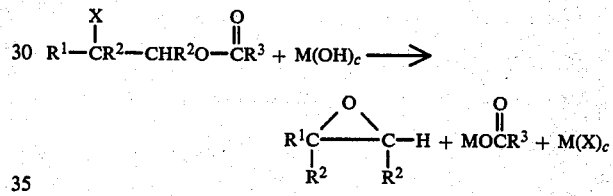

wherein $R^1$, $R^2$, $R^3$, X and c are as hereinbefore defined.

In the preferred embodiment wherein the carbonate starting material has a 2,3-dihaloalkyl moiety, the process is illustrated by equation 3,

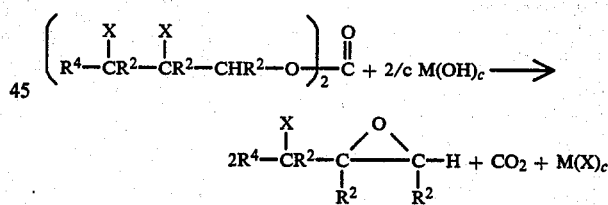

wherein $R^2$, $R^3$, $R^4$, X and c are as hereinbefore defined.

In this process, the carbonate starting materials are preferred over the ester starting materials because the by-products wherein the carbonates are the starting materials are $CO_2$ gas which evolves from the reaction mixture and an alkanol wherein a is 1.

In the process of this invention, the carbonate or ester is dissolved in a water-miscible alcohol. Any water-miscible alcohol is suitable for this reaction, preferred water-miscible alcohols are methanol, ethanol and propanol, with methanol being most preferred. In general, a sufficient amount of water-miscible alcohol is used to dissolve the carbonate or ester. Preferably, between about 200 and 1000 ml of alcohol per mole of carbonate or ester is used.

The aqueous solution of hydroxide can be any reasonable concentration of alkali metal hydroxide or alkaline earth metal hydroxide which results in the desired preparation of epoxides when such solution is contacted with the carbonate or ester in a water-miscible alcohol solution. It is preferable that the aqueous solution of hydroxide be between about 20 and 50 weight percent hydroxide. It is most preferred that the aqueous hydroxide solution contain between about 40 and 50 percent by weight of the hydroxide.

A sufficient amount of aqueous alkali metal hydroxide or alkaline earth metal hydroxide is contacted with the carbonate or ester dissolved in water-miscible alcohol so as to provide at least one equivalent of hydroxide per equivalent of carbonate or ester. The ratio of hydroxide to carbonate or ester is preferably between about 2.5:1 and 1:1, with a ratio of 1.5:1.1 being most preferred. Equivalent of carbonate or ester refers herein to an amount of ester or carbonate which will react with one mole of hydroxide moieties. In the embodiment wherein a bis(halo- or dihaloalkyl)carbonate is used, each mole of carbonate provides 2 equivalents.

This process can be run at a temperature of between about 0° C. and 70° C., with between about 40° C. and 60° C. being preferred, and between about 50° C. and 60° C. being most preferred. Above 70° C. there is significant danger that the epoxide moiety prepared will undergo hydrolysis and ethers will be formed. Below about 0° C. the reaction rate is very slow.

This process may be run at autogenous pressures.

When the carbonates are used, the reaction is complete when $CO_2$ evolution is completed.

The epoxides may be recovered from the reaction condition by methods well-known in the art. In one embodiment, the epoxide may be recovered by the reaction solution by adding excess water to the solution so as to create a two-phase system containing a water and organic phase, separating off the organic phase and distilling the epoxide from the reaction mixture. In another embodiment, the epoxide may be distilled directly from the reaction mixture.

Any reaction time which gives the desired yield is suitable for this process. Preferred reaction times are between about 2 and 8 hours, with between about 4 and 6 hours being most preferred.

The halogenated carbonates and esters useful in this reaction may be prepared by halogenating an unsaturated carbonate or ester. In general, an allyl or vinyl carbonate or ester can be contacted with a halogen or hydrogen halide at a temperature of 20° C. or lower in an organic solvent. Preferred organic solvents are the water-miscible alcohols as the reaction solution prepared containing the halogenated carbonate or ester can thereafter be used as the reaction solution which is contacted with the aqueous alkali metal hydroxide or alkaline earth metal hydroxide aqueous solution in the process described hereinbefore.

SPECIFIC EMBODIMENTS

The following examples are included for illustration, and do not limit the scope of the invention or the claims. All parts and percentages are by weight unless otherwise specified.

EXAMPLE 1

Preparation of bis(2,3-Dibromopropyl)carbonate (not an example of this invention)

Into a 500-ml flask are placed 36 g of diallyl carbonate (0.25 mole) and 200 ml of methylene chloride. This mixture is stirred and cooled in an ice water bath while 80 g of bromine (0.5 mole) is added dropwise. When the reaction is complete, the solvent is distilled off to give 114 g of oil, 98 percent yield of the desired product.

EXAMPLE 2

Preparation of 2,3-Dibromopropyl Acetate (not an example of this invention)

Into a 500-ml flask are placed 57 g of allyl acetate (0.57 mole) and 300 ml of methylene chloride. This mixture is stirred in an ice water bath while 91 g of bromine (0.57 mole) is added dropwise. When the reaction is complete some sodium carbonate and a little water are added and the mixture stirred until basic. The solids are filtered off and the low boilers removed by distillation under reduced pressure to give 144 g of oil, 97 percent yield. Nuclear magnetic resonance spectra shows this to be the desired 2,3-dibromopropyl acetate.

EXAMPLE 3

Preparation of (2,3-Dibromopropyl)methyl Carbonate (not an example of this invention)

Into a one-liter flask are placed 116 g of allyl methyl carbonate (1.0 mole) and 500 ml of methylene chloride. This mixture is stirred and cooled in an ice water bath while 160 g of bromine (1.0 mole) is added dropwise. When the reaction is complete, enough sodium carbonate and water are added to neutralize the mixture. The solids are filtered off and the low boilers removed by distillation to give 261 g of an oil, 95 percent yield.

EXAMPLE 4

Preparation of Epibromohydrin

In a 500-ml flask, 65 g of 2,3-dibromopropyl acetate (0.25 mole), 10 ml of water, 100 ml of methanol and 44 g of 50 percent sodium hydroxide (0.55 mole) are mixed giving an exothermic reaction. The mixture is then stirred at 60° C.–65° C. for 5 hours and allowed to cool. To this mixture is added 200 ml of water but no phasing occurs. The water phase is extracted twice with 150-ml portions of methylene chloride and these layers dried over sodium sulfate, filtered and distilled to give a 100 percent conversion of the 2,3-dibromopropyl acetate with a 38 percent yield of epibromohydrin.

EXAMPLE 5

Preparation of Epibromohydrin

Into a 500-ml flask are placed 65 g of 2,3-dibromopropyl acetate (0.25 mole) and 10 ml of water. This mixture is stirred while 44 g of a 50 percent aqueous solution of sodium hydroxide (0.55 mole) is added dropwise. An exothermic reaction takes place. After this addition, the mixture is stirred at 50° C. for 4 hours and allowed to cool. Another 20 ml of water is added and the product layer separates. The water phase is extracted with 100 ml of methylene chloride and this phase is added to the product phase and dried over sodium sulfate, filtered and distilled to give a 100 percent conversion and 38 percent yield of epibromohydrin. Other products are 2-bromo-1-propene and 2,3-dibromopropene.

EXAMPLE 6

Preparation of Epibromohydrin

Into a one-liter flask are placed 117 g of bis(2,3-dibromopropyl)carbonate (0.25 mole) and 100 ml of methanol. This mixture is stirred while 200 g of a 20 percent aqueous solution of sodium hydroxide (1.0 mole) is added dropwise. An exothermic reaction takes place. Solids are formed during this addition. The mixture is stirred for 6 hours. The solids are filtered off. The water phase is extracted with 200 ml of methylene chloride. The solids are treated with 150 ml of water and this phase extracted with 150 ml of methylene chloride. The two methylene chloride phases are combined, dried over sodium sulfate, filtered and distilled to give an 81 percent conversion of the carbonate and a 45 percent yield of epibromohydrin. Some other halogenated products are also obtained.

EXAMPLE 7

Preparation of Epibromohydrin

Into a 500-ml flask are placed 117 g of bis(2,3-dibromopropyl)carbonate (0.25 mole) and 200 ml of methanol. This mixture is stirred and 60 g of a 50 percent aqueous solution of sodium hydroxide (0.75 mole) is added in one portion. An exotherm to 72° C. is obtained and solids formed. The mixture is stirred for 3 hours and poured into 400 ml of water. The resulting product phase is extracted twice with 200-ml portions of methylene chloride. These product layers are dried over sodium sulfate, solids filtered off and distilled to give almost complete conversion of the carbonate and a 58 percent yield of epibromohydrin. Some 2,3-dibromopropene is also formed.

EXAMPLE 8

Preparation of Epibromohydrin

Into a one-liter flask are placed 116 g of bis(2,3-dibromopropyl)carbonate (0.25 mole), 50 ml of methanol, 37 g of water and 37 g of calcium hydroxide (0.5 mole). This mixture is stirred and heated to 40° C. for 4 hours and at 60° C. for 4 hours. After cooling 200 ml of methylene chloride and 100 ml of water are added and the mixture stirred. The product is filtered through some filter cell and the product phase separated, dried over sodium sulfate, filtered and distilled to give a 100 percent conversion of the carbonate and a 50 percent yield of epibromohydrin. A 28 percent yield of 2,3-dibromo-1-propanol is also obtained. No detectable dibromopropenes are obtained.

EXAMPLE 9

Preparation of Epibromohydrin using a 1,2-Dichloroethane Solvent (not an example of this invention)

Into a one-liter flask are placed 36 g of bis(allyl)carbonate (0.25 mole) and 250 ml of 1,2-dichloroethane. This mixture is stirred and cooled in an ice water bath while 80 g of bromine (0.5 mole) is added dropwise. When the reaction is complete, an aqueous solution of 25 g of sodium hydroxide (0.63 mole) and 13 g of sodium carbonate in 160 ml of water is added. The mixture is then heated to 60° C.-65° C. for 4 hours. After cooling, the product layer is separated, dried over sodium sulfate and distilled to give very little conversion of the bis(2,3-dibromopropyl)carbonate. Very little epibromohydrin is obtained. Some 2,3-dibromo-1-propanol is obtained.

EXAMPLE 10

Preparation of Epibromohydrin

Into a 500-ml flask are placed 36 g of bis(allyl carbonate (0.25 mole) and 100 ml of methanol. This mixture is stirred and cooled in an ice water bath while 80 g of bromine (0.5 mole) is added dropwise. When this reaction is complete, 11 ml of water is added and the mixture stirred while 44 g of a 50 percent aqueous solution of sodium hydroxide (0.55 mole) is added at such a rate so as to maintain reaction temperatures below 55° C. The mixture is then heated to 60° C. for 4 hours and allowed to cool. To this mixture is added 250 ml of water and the resulting water phase is extracted twice with 150-ml portions of methylene chloride. The products are combined and dried over sodium sulfate, filtered and distilled to give a 100 percent conversion of carbonate and 54 percent yield of epibromohydrin. No detectable dibromopropene appeared to be formed.

EXAMPLE 11

Preparation of Epibromohydrin (not an example of this invention)

Into a 500-ml flask are placed 117 g of bis(2,3-dibromopropyl)carbonate (0.25 mole) and 60 g of a 50 percent aqueous solution of sodium hydroxide (0.75 mole). An exotherm to 105° C. takes place. The mixture is cooled to 40° C. and held there for 2 hours. After cooling, 250 ml of water is added and the mixture stirred. The water phase is extracted twice with 200-ml portions of methylene chloride. These phases are dried over sodium sulfate, filtered and distilled to give a 60 percent conversion of the carbonate and a 30 percent yield of epibromohydrin. Some dibromopropene is also obtained.

EXAMPLE 12

Preparation of Epibromohydrin using a 1,2-Dichloroethane Solvent (not an example of this invention)

Into a one-liter flask are placed 58 g of allyl methyl carbonate (0.5 mole) and 250 ml of 1,2-dichloroethane. This mixture is stirred and cooled in an ice water bath while 80 g of bromine (0.5 mole) is added dropwise. When this reaction is complete, an aqueous solution of 25 g sodium hydroxide (0.63 mole) and 13 g of sodium carbonate in 160 ml of water is added. The mixture is then slowly heated to 60° C.-65° C. while some methanol (by-product) distills off. The mixture is then heated to 65° C. for 5 hours. After cooling, the product layer is separated and dried over sodium sulfate, filtered and distilled to give a 100 percent conversion of carbonate but only a 6 percent yield of epibromohydrin.

EXAMPLE 13

Preparation of Epibromohydrin

Into a 500-ml flask are placed 70 g of (2,3-dibromopropyl)methyl carbonate (0.25 mole), 150 ml of methanol and 100 g of a 20 percent sodium hydroxide water solution (0.5 mole). Considerable solids are formed. The mixture is stirred at reflux for 2 hours and allowed to cool. No apparent phasing occurs after 200 ml of water is added. The product is extracted twice with 200-ml portions of methylene chloride. These phases are combined, dried over sodium sulfate, filtered and distilled to give a 100 percent conversion of the carbonate with a 54 percent yield of epibromohydrin.

EXAMPLE 14

Preparation of Ethylene Oxide and Propylene Oxide

Into a 500-ml flask are placed 61 g of (2-bromopropyl) (2-chloroethyl)carbonate (0.25 mole) and 100 ml of methanol. The flask is equipped with a dry ice/methylene chloride trap and trap for gases. The mixture is stirred while 100 g of a 20 percent aqueous solution of sodium hydroxide (0.55 mole) is added dropwise. An exotherm to 40° C. takes place. The mixture is then stirred at 75° C. for 4 hours. The low boiling products are collected and 13 g are proved to be a 67/33 percent mixture of propylene oxide and ethylene oxide by nuclear magnetic resonance and gas-liquid chromatography analysis. This is a 51+ percent yield of products. The water/methanol phase is washed twice with 100-ml portions of water and extracted twice with 100-ml portions of ether. The ether phases are dried over sodium sulfate and filtered. The low boilers are removed to give an oil that is mostly methanol. A 100 percent conversion of the carbonate takes place.

What is claimed is:

1. A process for the preparation of an epoxide which comprises contacting a 2-haloalkyl or 2,3-dihaloalkyl carbonate, or a bis(2-haloalkyl- or 2,3-dihaloalkyl)carbonate dissolved in a water-miscible alcohol with a sufficient amount of an aqueous solution of an alkali metal hydroxide or alkaline earth metal hydroxide to provide at least one equivalent of alkali metal or alkaline earth metal hydroxide per equivalent of carbonate, at a temperature of between about 0° C. and 70° C. under conditions such that an epoxide is prepared, said carbonates corresponding to the formula:

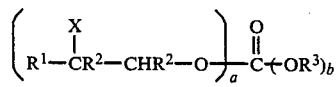

wherein $R^1$ is separately in each occurrence

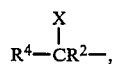

hydrogen, $C_{1-20}$hydrocarbyl or $C_{2-20}$hydrocarbyloxyhydrocarbyl;

$R^2$ is separately in each occurrence hydrogen or $C_{1-20}$hydrocarbyl;

$R^3$ is separately in each occurrence $C_{1-20}$hydrocarbyl;

$R^4$ is separately in each occurrence hydrogen, $C_{1-20}$hydrocarbyl or $C_{1-20}$hydrocarbyloxyhydrocarbyl;

X is separately in each occurrence chlorine, bromine or iodine;

a is 1 or 2; and b is 0 or 1;

with the proviso that the sum of a and b is 2.

2. The process of claim 1 wherein
$R^1$ is

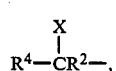

hydrogen, $C_{1-20}$ alkyl, $C_{6-20}$ aryl, $C_{7-20}$ alkaryl, $C_{7-20}$ aralkyl or $C_{2-20}$ alkoxyalkyl;

$R^2$ is hydrogen or $C_{1-20}$ alkyl;

$R^3$ is $C_{1-20}$ alkyl, $C_{6-20}$ aryl, $C_{7-20}$ alkaryl or $C_{7-20}$ aralkyl;

$R^4$ is hydrogen, $C_{1-20}$ alkyl, $C_{6-20}$ aryl, $C_{7-20}$ alkaryl, $C_{7-20}$ aralkyl or $C_{2-20}$ alkoxyalkyl; and X is chlorine or bromine.

3. The process of claim 3 wherein
$R^1$ is

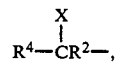

hydrogen, $C_{1-10}$ alkyl, $C_{6-10}$ aryl, $C_{7-10}$ alkaryl, $C_{7-10}$ aralkyl or $C_{2-10}$ alkoxyalkyl;

$R^2$ is hydrogen or $C_{1-3}$ alkyl;

$R^3$ is $C_{1-10}$ alkyl, $C_{6-10}$ aryl, $C_{7-10}$ alkaryl or $C_{7-10}$ aralkyl; and $R^4$ is hydrogen, $C_{1-10}$ alkyl, $C_{6-10}$ aryl, $C_{7-10}$ alkaryl, $C_{7-10}$ aralkyl or $C_{2-10}$ alkoxyalkyl.

4. The process of claim 3 wherein
$R^1$ is

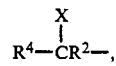

hydrogen, $C_{1-4}$ alkyl, phenyl or benzyl;

$R^2$ is hydrogen or methyl;

$R^3$ is $C_{1-3}$ alkyl, phenyl or benzyl; and $R^4$ is hydrogen, $C_{1-4}$ alkyl, phenyl or benzyl.

5. The process of claim 4 wherein
$R^1$ is

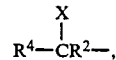

hydrogen or methyl;

$R^2$ is hydrogen; and $R^4$ is hydrogen or methyl.

6. The process of claim 2 wherein
$R^1$ is

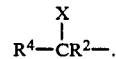

7. The process of claim 1 wherein between about 1 and 2.5 equivalents of hydroxide are contacted with each equivalent of carbonate.

8. The process of claim 7 wherein the hydroxide is an alkali metal hydroxide.

9. The process of claim 8 wherein the alkali metal hydroxide is sodium hydroxide or potassium hydroxide.

10. The process of claim 9 wherein the temperature is between about 50° C. and 60° C.

11. The process of claim 10 wherein the water-miscible alcohol is methanol, ethanol or propanol.

12. The process of claim 10 wherein the water-miscible alcohol is methanol.

13. The process of claim 1 wherein the epoxide prepared corresponds to the formula

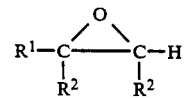

wherein

R¹ is

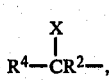

hydrogen, $C_{1-20}$ hydrocarbyl or $C_{2-20}$ hydrocarbyloxyhydrocarbyl;

R² is hydrogen or $C_{1-20}$ hydrocarbyl;

R⁴ is hydrogen, $C_{1-20}$ hydrocarbyl or $C_{1-20}$ hydrocarbyloxyhydrocarbyl; and X is chlorine, or bromine.

14. A process for the preparation of α-halo-substituted epoxides which comprises contacting a 2,3-dihaloalkyl carbonate, or a bis(2,3-dihaloalkyl)carbonate dissolved in a water-miscible alcohol with a sufficient amount of an aqueous solution of an alkali metal or alkaline earth metal hydroxide to provide at least one equivalent of alkali metal or alkaline earth metal hydroxide per equivalent of carbonate, at a temperature of between about 0° C. and 70° C. under conditions such that an α-halo-substituted epoxide is prepared, said carbonates corresponding to the formula:

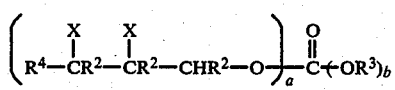

wherein

R² is separately in each occurrence hydrogen or $C_{1-20}$ hydrocarbyl;

R³ is separately in each occurrence $C_{1-20}$ hydrocarbyl;

R⁴ is separately in each occurrence hydrogen, $C_{1-20}$ hydrocarbyl or $C_{2-20}$ hydrocarbyloxyhydrocarbyl;

X is separately in each occurrence chlorine, bromine or iodine;

a is 1 or 2; and b is 0 or 1;

with the proviso that the sum of a and b is 2.

15. A process for the preparation of an epihalohydrin which comprises contacting a 2,3-dihalopropyl carbonate, or a bis(2,3-dihalopropyl)carbonate dissolved in a water-miscible alcohol with a sufficient amount of an aqueous solution of an alkali metal or alkaline earth metal hydroxide to provide at least one equivalent of alkali metal or alkaline earth metal hydroxide per equivalent of carbonate, at a temperature of between about 0° C. and 70° C. under conditions such that an epihalohydrin is prepared.

* * * * *